US00PP11873P2

(12) United States Plant Patent
Fruehwirth

(10) Patent No.: US PP11,873 P2
(45) Date of Patent: May 15, 2001

(54) POINSETTIA PLANT NAMED 'ECKABIR'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/431,248

(22) Filed: Nov. 1, 1999

(51) Int. Cl.[7] ..... A01H 5/00

(52) U.S. Cl. ..... Plt./307
(58) Field of Search ..... Plt./307

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Poinsettia plant named 'Eckabir', characterized by its bright red bracts; response time about 9.5 weeks; freely branching, upright and spreading plant habit; and good postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Eckabir'.

The new cultivar is a product of a planned breeding program conducted by the Inventor in Encinitas, Calif. The objective of the program is to create new Poinsettia cultivars having interesting bract and leaf display, color and form; strong and freely branching stems; and good post-production longevity.

The new cultivar originated from a cross made by the Inventor of the Poinsettia cultivar '559', disclosed in U.S. Plant Pat. No. 8,773, as the male, or pollen parent, with an unnamed proprietary Poinsettia selection as the female, or seed parent.

The cultivar 'Eckabir' was discovered and selected by the Inventor as a flowering plant within the progeny of the stated cross in a controlled environment in Encinitas, Calif. in December, 1995.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckabir'. These characteristics in combination distinguish 'Eckabir' as a new and distinct cultivar:

1. Bright red bracts.
2. Response time about 9.5 weeks.
3. Upright and spreading plant habit.
4. Vigorous.
5. Freely branching habit.
6. Good postproduction longevity.

Plants of the new Poinsettia can be compared to plants of the male parent, the cultivar '559'. However, in side-by-side comparisons conducted in Encinitas, Calif., plants of the new Poinsettia differed from plants of '559' in the following characteristics:

1. Plants of the new Poinsettia are slightly taller, more outwardly spreading and more vigorous than plants of '559'.
2. Plants of the new Poinsettia have slightly larger leaves and longer petioles than plants of '559'.
3. Plants of the new Poinsettia have larger and flatter inflorescences than plants of '559'.
4. Plants of the new Poinsettia have fewer but larger bracts than plants of '559'.
5. Bracts of the new Poinsettia are held more upright than bracts of '559'.
6. Plants of the new Poinsettia flower earlier than plants of '559'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph at the top of the first sheet comprises a side perspective view of a typical plant of 'Eckabir'.

The photograph at the bottom of the first sheet comprises a top perspective view of a typical plant of 'Eckabir'.

The photograph on the second sheet is a close-up view of typical bracts and leaves of 'Eckabir' (left) and '559' (right). Bract and foliage colors in the photographs may differ from actual colors due to light reflectance.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a glass-covered greenhouse with day temperatures ranging from 21 to 27° C., night temperatures ranging from 18 to 20° C., and light levels about 4,000 foot-candles. Plants were grown in 16-cm pots, pinched one time, and flowered under naturally lengthening nights during the fall/early winter.

In the following description, color references are made to The Royal Horticultural Society Colour Chart except where general terms of ordinary dictionary significance are used.

Botanical classification: *Euphorbia pulcherrima* Willd. 'Eckabir'.

Parentage:

*Male parent.*—*Euphorbia pulcherrima* Willd. '559', disclosed in U.S. Plant Pat. No. 8,773.

*Female parent.*—Unnamed propriety selection of *Euphorbia pulcherrima* Willd.

Propagation:

*Type cutting.*—Terminal cuttings.

*Time to initiate roots.*—Summer: About 7 days at 24° C. Winter: About 10 days at 22° C.

*Time to develop roots.*—Summer: About 26 days at 24° C. Winter: About 26 days at 22° C.

*Rooting habit.*—Freely branching, becoming fibrous with development.

Plant description:

*Plant form.*—Inverted triangle.

*Growth habit.*—Upright and spreading. Freely branching. Branching is enhanced by removing the shoot apex.

*Plant vigor.*—High.

*Plant height.*—About 31 cm.

*Crop time.*—From unrooted cuttings to a flowering plant in a 16-cm container, about 17 to 18 weeks are required.

*Stem description.*—Strong, thick stems. Number of lateral branches: About six lateral branches are formed after removal of the terminal apex. Lateral branch length: About 26 cm. Internode length: About 2.75 cm. Stem color: 146A to 146B.

*Foliage description.*—Quantity of leaves per lateral branch: About 8. Length: About 11.75 cm. Width: About 8 cm. Shape: Ovate to occasionally lobed. Apex: Acuminate. Base: Rounded to acute. Margin: Entire. Texture: Smooth; very sparse pubescence on lower surface. Color: Young foliage, upper surface: 147A. Young foliage, lower surface: 147B. Mature foliage, upper surface: 147A. Mature foliage, lower surface: 147B. Venation, upper surface: 147C. Venation, lower surface: 147D. Petiole: Length: About 5.2 cm. Diameter: About 2 mm. Color: 180A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long night conditions. Response time is about 9.5 weeks.

*Quantity of inflorescences.*—One per lateral branch, usually about six per plant.

*Inflorescence size including bracts.*—Diameter: About 30 cm. Height (depth): About 3.5 cm.

*Flower bracts.*—Quantity of flower bracts per inflorescence: Usually about 10 primary bracts and about 6 smaller secondary bracts per inflorescence. Length, largest bracts: About 14 cm. Width, largest bracts: About 11 cm. Shape: Ovate to lobed. Apex: Acuminate. Base: Acute. Margin: Entire. Texture: Smooth. Aspect: Held somewhat upright. Color: Developing, upper surface: 45A. Developing, lower surface: 45B. Mature, upper surface: 45A to 45B, becoming slightly lighter than 45B with subsequent development. Mature, lower surface: 45C.

*Cyathia.*—Quantity: Usually about 11 per corymb. Diameter of cyathia cluster: About 2 by 2 cm. Length: About 1.2 cm. Width: About 6 mm. Color: Immature: 144A. Mature: 144B. Peduncle: Length: About 2 mm. Aspect: Strong, erect. Color: 144B. Stamens: Stamen number: Six to ten true stamen with numerous stamenodes per cyathium. Anther length: About 1 mm. Anther shape: Oval. Anther color: 45A. Amount of pollen: Scarce. Pollen color: 7A. Pistils: No pistillate flowers observed. Nectary color: 14A.

Disease resistance: Plants of the new Poinsettia have been observed to be somewhat resistant to Botrytis.

Postproduction longevity: Good; generally plants maintain good substance and bract color for about six to eight weeks under interior conditions.

It is claimed:

1. A new and distinct cultivar of Poinsettia plant named 'Eckabir', as illustrated and described.

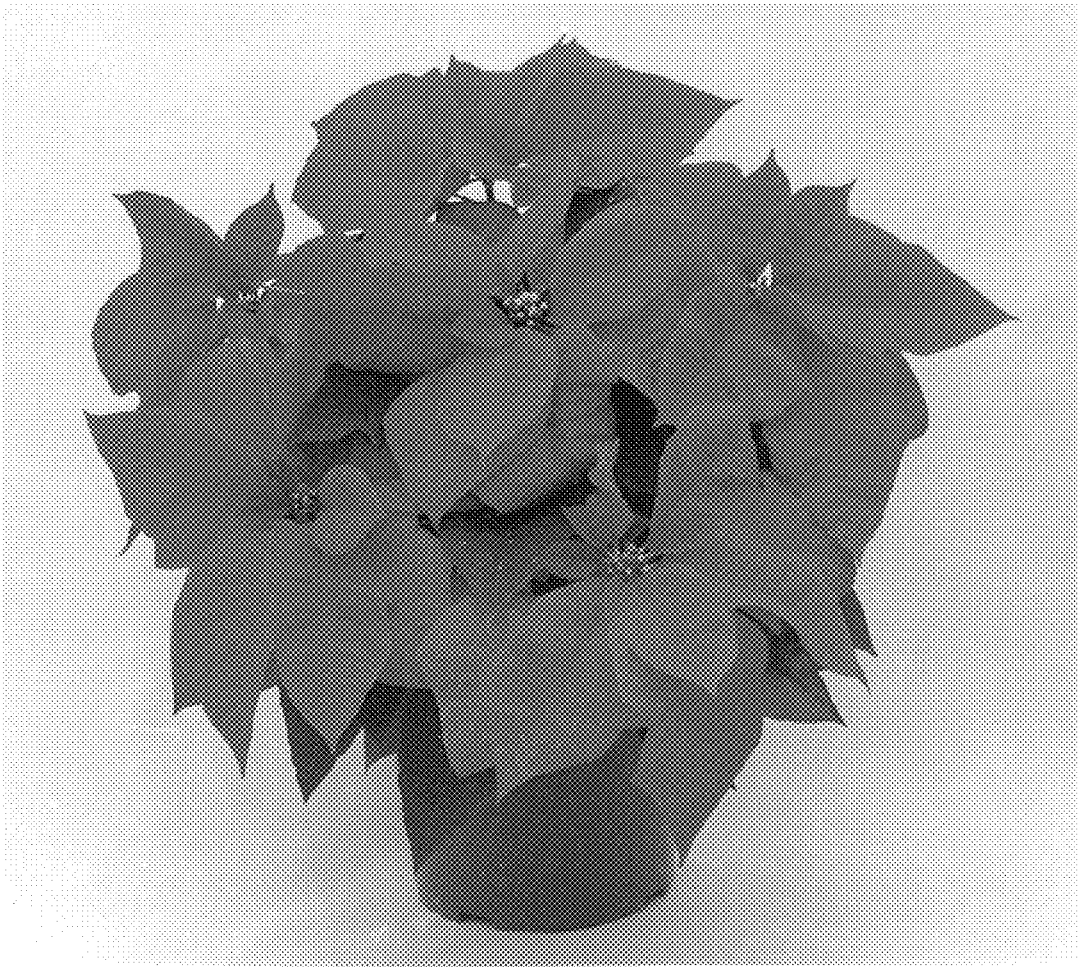
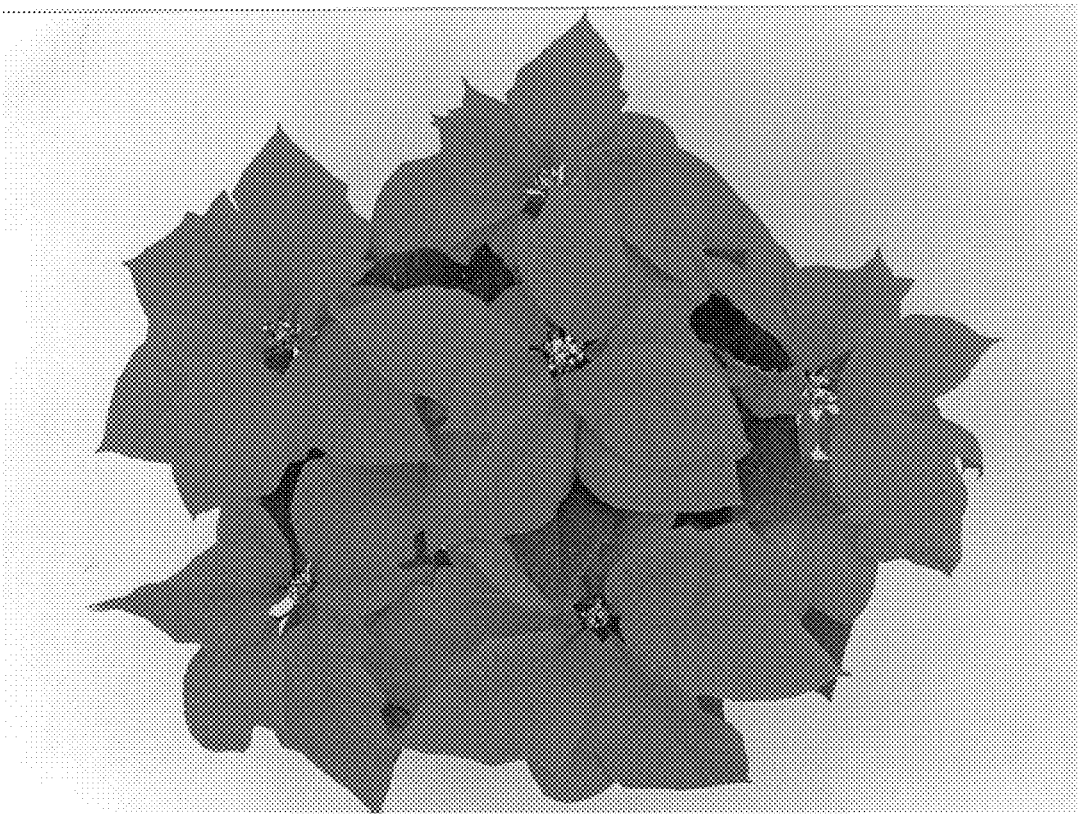

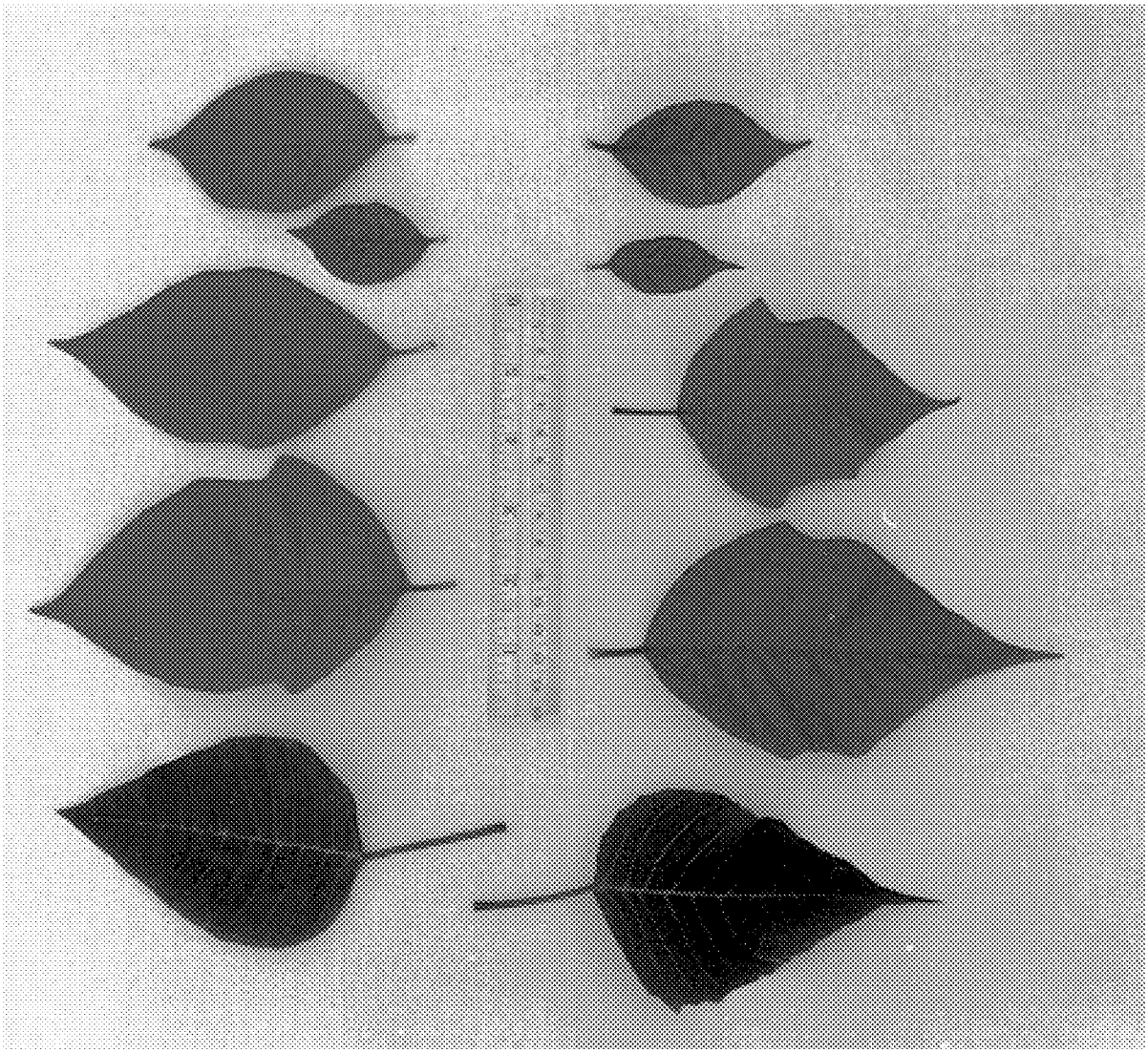

* * * * *